United States Patent [19]
Butler et al.

[11] Patent Number: 4,745,123
[45] Date of Patent: May 17, 1988

[54] SUBSTITUTED TETRAHYDRO-3-PYRIDINE-CARBOXYLIC ACID, ESTER, AND AMIDE CHOLINERGIC AGENTS

[75] Inventors: Donald E. Butler, Holland, Mich.; John H. Dodd, Lebanon, N.J.; Walter H. Moos; Haile Tecle, both of Ann Arbor, Mich.

[73] Assignee: Warner-Lambert Company, Morris Plains, N.J.

[21] Appl. No.: 830,035

[22] Filed: Feb. 18, 1986

[51] Int. Cl.[4] .................. A61K 31/44; A61K 31/445; C07D 211/42; C07D 207/12

[52] U.S. Cl. .................... 514/356; 540/524; 544/58.4; 544/131; 544/365; 546/194; 546/275; 546/281; 546/284; 546/316; 546/318; 546/321; 546/322

[58] Field of Search .................. 546/322; 514/356

[56] References Cited

U.S. PATENT DOCUMENTS

| | | | |
|---|---|---|---|
| 4,064,253 | 12/1977 | Khoe | 514/356 |
| 4,096,268 | 6/1978 | Tamura et al. | 546/322 X |
| 4,238,488 | 12/1980 | Howe et al. | 546/322 X |
| 4,383,999 | 5/1983 | Bondinell et al. | 514/356 X |
| 4,467,095 | 8/1984 | Treves et al. | 546/342 |

Primary Examiner—Joseph Paul Brust
Attorney, Agent, or Firm—Jerry F. Janssen

[57] ABSTRACT

Certain substituted 1,2,3,6-tetrahydro- and 1,2,5,6-tetrahydropyridine-3-carboxylic acids, esters, and amides possessing muscarinic binding activity, having utility for the treatment of the symptoms of senile cognitive decline disclosed. Pharmaceutical compositions and a pharmaceutical method of treatment are also disclosed.

21 Claims, No Drawings

SUBSTITUTED TETRAHYDRO-3-PYRIDINE-CARBOXYLIC ACID, ESTER, AND AMIDE CHOLINERGIC AGENTS

BACKGROUND OF THE INVENTION

The present invention relates to compounds, pharmaceutical compositions, and to a pharmaceutical method of treatment. More particularly, this invention is concerned with a class of substituted tetrahydro-3-pyridinecarboxylic acids, esters, and amides, pharmaceutical compositions containing the compounds, and to a pharmaceutical method of treatment.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common causes of mental deterioration in the elderly. It has been estimated that at least ten percent of persons over sixty years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia for example, the level of the enzyme choline acetyltransferase (CAT) can be reduced by as much as ninety percent. (See Davies et al., *The Lancet,* 1976 (Vol. 2): 1403; Perry et al., *J. Neurol. Sci.,* 34: 247–265 (1977); and White et al., *The Lancet,* 1977 (Volume 1): 668–670).

Since CAT catalyzes the synthesis of acetylcholine from its precursors choline and acetyl coenzyme A, the loss of CAT reflects the loss of cholinergic, or acetylcholine-releasing, nerve endings in the hippocampus and cerebral cortex. There is abundant evidence that cholinergic terminals in the hippocampus are critically important for memory formation.

The cholinergic hypothesis suggests that drugs which restore acetylcholine levels or which mimic the action of acetylcholine (cholinomimetic) are effective in correcting this deficit in neurotransmitter chemical and provide treatment of the memory impairment symptom of cerebral insufficiency.

It has been known for some time that the natural alkaloid, muscarine, has the ability to act relatively selectively at autonomic effector cells to produce qualitatively the same effects as acetylcholine. Two related alkaloids, pilocarpine and arecoline, have the same principal sites of action as muscarine and acetylcholine and are thus classified as having "muscarinic" action. Although these naturaly occurring alkaloids are of great value as pharmacological tools, present clinical use is largely restricted to the use of pilocarpine as a miotic agent.

Arecoline (the methyl ester of 1,2,5,6-tetrahydro-1-methyl-3-pyridinecarboxylic acid) is the chief alkaloid found in betel nuts (*Areca catechu*). Betel nuts have been chewed by natives of the East Indies since early times as a euphoretic. The present pharmaceutical utility of arecoline, however, has been limited to its use as a veterinary anthelmintic agent. Recently it has been demonstrated that arecoline is effective in ameliorating some of the symptoms of cognitive disorders in patients clinically diagnosed as having presenile primary degernerative dementia. Significant improvement was observed in a test of picture recognition after administration of arecoline to patients in a double blind study. (See Christie et al., *Brit. J. Psychiatry,* 138: 46–50 (1981)).

SUMMARY OF THE INVENTION

In its broadest aspect, the present invention provides compounds having structural formula 1

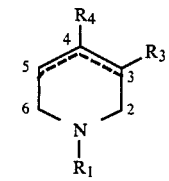

wherein the dashed lines indicate the presence of only one carbon-carbon double bond either between carbon atoms numbers 3 and 4 or between carbon atoms numbers 4 and 5. The substituent group $R_1$ is hydrogen; straight or branched alkyl of from one to six carbon atoms; straight or branched alkenyl of from one to six carbon atoms; alkoxycarbonyl of from two to five carbon atoms; cycloalkyl of from four to eight carbon atoms; phenylalkyl wherein the alkyl portion is straight or branched of from one to six carbon atoms, and the phenyl ring may be unsubstituted or substituted with halogen, hydroxy, alkyl of from one to six carbon atoms, or alkyloxy of from one to four carbon atoms.

The group $R_3$ is —COOR where R is hydrogen, straight or branched alkyl of from one to six carbon atoms; straight or branched alkenyl of from one to six carbon atoms; cycloalkyl of from three to eight carbon atoms; phenyl; phenyl substituted with halogen, hydroxy, nitro, amino, acylamino in which the acyl group contains from two to six carbon atoms, alkyl of from one to four carbon atoms, alkyloxy of from one to four carbon atoms; phenylalkyl wherein the alkyl portion is straight or branched of from one to six carbon atoms, and the phenyl ring may be unsubstituted or substituted with halogen, hydroxy, alkyl of from one to six carbon atoms, or alkyloxy of from one to four carbon atoms.

The substituent group $R_3$ may also be —CONR'R" where R' and R" are independently hydrogen or alkyl of from one to four carbon atoms. Alternatively, R' is hydrogen and R" is cycloalkyl of from three to eight carbon atoms; benzyloxy; phenylalkyl wherein the alkyl portion is straight or branched of from one to six carbon atoms, and the phenyl ring may be unsubstituted or substituted with halogen, hydroxy, alkyl of from one to six carbon atoms, or alkyloxy of from one to four carbon atoms.

The substituent groups R' and R" when taken together with the nitrogen atom to which they are attached form a pyrrolidinyl, piperidinyl, 4-(diphenylmethylenepiperazinyl, azepinyl, morpholinyl, thiomorpholinyl, isoxazolyl, piperazinyl, or 4-alkylpiperazinyl ring where the alkyl group may be straight or branched alkyl of from one to six carbon atoms.

The substituent group $R_4$ is straight or branched alkyl of from one to six carbon atoms; straight or branched alkenyl of from one to six carbon atoms; cycloalkyl of from three to eight carbon atoms; 2- or 3-thienyl; phenyl; phenyl substituted with halogen, hydroxy, nitro, amino, acylamino in which the acyl group contains from two to six carbon atoms, alkyl of from one to four carbon atoms, alkyloxy of from one to four carbon atoms; phenylalkyl wherein the alkyl portion is straight or branched of from one to six carbon atoms, and the phenyl ring may be unsubstituted or substituted with halogen, hydroxy, alkyl of from one to six carbon atoms, or alkyloxy of from one to four carbon atoms; and the pharmaceutically acceptable salts thereof.

In another aspect, the present invention provides pharmaceutical compositions useful in alleviating the symptoms of senile cognitive decline comprising an effective amount of a compound as described above in combination with a pharmaceutically acceptable carrier.

In yet another aspect, the present invention provides a method of alleviating the symptoms of cognitive decline in the elderly comprising administering to a patient in need of such treatment an effective amount of a pharmaceutical composition as defined above.

DETAILED DESCRIPTION

Compounds of the present invention are ester or amide derivatives of 1,2,5,6-tetrahydropyridine-3-carboxylic acid or of (±)-1,2,3,6-tetrahydropyridine-3-carboxylic acid possessing cholinergic activity.

The compounds may be substituted on the ring nitrogen atom with alkyl or alkenyl groups or with groups such as phenylalkyl, or substituted phenylalkyl.

Position 3 of the tetrahydropyridine ring system is substituted with an acid group, an ester group or an amide group. Various esters contemplated within the scope of the invention are as detailed above, with alkyl, cycloalkyl and benzyl esters being preferred.

Preferred amide compounds of the present invention include N-alkyl-, N,N-dialkyl-, N-benzyl-, and N-cycloalkylamides, as well as those in which the amide nitrogen atom forms part of a piperidinyl or isoxazolyl ring.

Position 4 of the tetrahydropyridine ring is preferably substituted with phenyl, substituted phenyl, or 2- or 3-thienyl, with phenyl being most preferred.

As used throughout this specification and the appended claims, the term "alkyl" denotes a straight or branched hydrocarbon group derived from an alkane by the removal of a single hydrogen atom.

"Cycloalkyl of from four to eight carbon atoms" includes cyclobutyl, cyclopentyl, cyclohexyl, cycloheptyl, and cyclooctyl.

The term "alkenyl" means a straight or branched hydrocarbon group derived from an alkene by the removal of a single hydrogen atom.

The term "alkoxy" denotes an alkyl group, as defined above, attached to the parent molecular moiety through an oxygen atom.

The term "alkoxycarbonyl" denotes

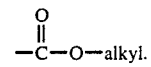

"Halogen" means fluorine, chlorine, bromine, or iodine. The term "phenylalkyl" denotes a benzene ring, attached through a branched or unbranched alkyl group to the parent molecular moiety.

In one preferred aspect, the present invention provides compounds of structural formula 2

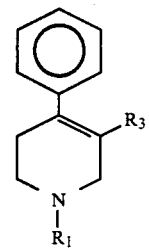

where $R_1$ and $R_3$, are as defined above.

In another preferred aspect, the present invention provides compounds of structural formula 3

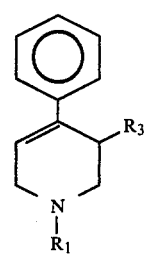

where $R_1$ and $R_3$ are as defined above.

Particularly preferred compounds of the present invention are those of structure 1 above where $R_1$ is alkyl of from one to six carbon atoms, $R_3$ is alkoxycarbonyl and $R_4$ is phenyl.

It will be evident to one skilled in the art that when the double bond of compounds of the present invention is between carbon atoms 4 and 5 in structural formula 1 above, carbon atom number 3 is an asymmetric center, and such compounds can exist in isomeric 3R and 3S forms. Individual stereoisomers can be separated from mixtures of the two forms by formation and resolution of diastereomeric derivatives followed by resolution, chromatography on stereospecific columns, or other techniques known to the art. The present invention contemplates the individual 3R and 3S stereoisomers of 1,2,3,6-tetrahydropyridine derivatives of formula 1, as well as mixtures thereof.

Examples of preferred compounds of the present invention are:

1-Ethyl-1,2,5,6-tetrahydro-4-phenyl-3-pyridinecarboxylic acid.

1,2,5,6-Tetrahydro-4-phenyl-1-propyl-3-pyridinecarboxylic acid.

1,2,5,6-Tetrahydro-4-phenyl-1-propyl-3-pyridinecarboxylic acid, methyl ester.

1,2,5,6-Tetrahydro-4-phenyl-1-propyl-3-pyridinecarboxylic acid, phenylmethyl ester.

1,2,5,6-Tetrahydro-4-phenyl-1-propyl-3-pyridinecarboxylic acid, 1-phenylethyl ester.

1-Ethyl-1,2,5,6-tetrahydro-4-phenyl-N-(phenylmethyl)-3-pyridinecarboxamide.

1,2,5,6-Tetrahydro-4-phenyl-1-(phenylmethyl)-3-pyridinecarboxylic acid, methyl ester.

1-Ethyl-1,2,5,6-tetrahydro-4-phenyl-3-pyridinecarboxylic acid, cyclopentyl ester.

1,2,5,6-Tetrahydro-4-phenyl-1-(2-propenyl)-3-piperidinecarboxylic acid, phenylmethyl ester.

1-Ethyl 1,2,5,6-tetrahydro-N-methyl-4-phenyl-3-pyridinecarboxamide.

1-Ethyl-1,2,5,6-tetrahydro-N,N-dimethyl-4-phenyl3-pyridinecarboxamide.

1,2,5,6-Tetrahydro-4-phenyl-N-(phenylmethoxy)-1-propyl-3-pyridinecarboxamide.

1,2,5,6-Tetrahydro-4-phenyl-3-pyridinecarboxylic acid, methyl ester.

1-[(1-Ethyl-1,2,5,6-tetrahydro-4-phenyl-3-pyridinyl)-carbonyl]piperidine.

4-(Diphenylmethylene)-1-[(1-ethyl-1,2,5,6-tetrahydro-4-phenyl-3-pyridinyl)carbonyl]piperidine.

2-[(1-Ethyl-1,2,5,6-tetrahydro-4-phenyl-3-pyridinyl)-carbonyl]isoxazolidine.

1-Cyclopentyl-1,2,5,6-tetrahydro-4-phenyl-3-pyridinecarboxylic acid, methyl ester.

5,6-Dihydro-4-phenyl-1,3(2H)-pyridinedicarboxylic acid, 1-ethyl, 3-methyl ester.

4-Butyl-1,2,5,6-tetrahydro-1-propyl-3-pyridinecarboxylic acid, methyl ester.

4-(3,4-Dichlorophenyl)-1-ethyl-1,2,5,6-tetrahydro-3-pyridinecarboxylic acid, methyl ester.

1-Ethyl-1,2,5,6-tetrahydro-4-(2-thienyl)-3-pyridinecarboxylic acid, methyl ester.

(±)-1-Ethyl-1,2,3,6-tetrahydro-4-phenyl-3-pyridinecarboxylic acid, phenylmethyl ester.

(±)-1,2,3,6-Tetrahydro-1-methyl-4-phenyl-3- pyridinecarboxylic acid, methyl ester.

(±)-1,2,3,6-Tetrahydro-4-phenyl-1-(2-phenylethyl)-3-pyridinecarboxylic acid.

(±)-1-Ethyl-1,2,3,6-tetrahydro-4-phenyl-3-pyridinecarboxylic acid.

(±)-1-Ethyl-1,2,3,6-tetrahydro-4-phenyl-3-pyridinecarboxylic acid, cyclohexyl ester.

(±)-1,2,3,6-Tetrahydro-1-(cyclopentyl)-4-phenyl-3-pyridinecarboxylic acid, methyl ester.

4-Butyl-1,2,5,6-tetrahydro-1-propyl-3-pyridinecarboxylic acid, methyl ester.

1-Ethyl-1,2,5,6-tetrahydro-4-(2-thienyl)-3-pyridinecarboxylic acid, methyl ester.

(±)-1-Ethyl-1,2,3,6-tetrahydro-4-(4-nitrophenyl)-3-pyridinecarboxylic acid, methyl ester.

(±)-1-Ethyl-1,2,3,6-tetrahydro-4-(2-thienyl)-3-pyridinecarboxylic acid, methyl ester.

The compounds of the present invention may be prepared by the method detailed in the Reaction Sequence and illustrated by Examples 1-98 below. Specific preparative examples are given as illustrative of the synthetic procedures employed.

The known 4-substituted-3-(4,4-dimethylisoxazol-2-yl)pyridines, 4, (see A. E. Hauck et al., *J. Chem. Soc., Perkin I,* (1980) 2070-2076) are hydrolyzed in aqueous acid to produce the 4-substituted nicotinic acid compounds, 5. The 4-phenyl- compounds in which the phenyl group is substituted by hydroxy may be prepared by prior formation of the corresponding methoxy compounds followed by heating with hydrobromic acid to convert the methoxyphenyl compounds to the hydroxyphenyl compounds.

Similarly, the 4-phenyl compounds in which the phenyl group is substituted with amino may be prepared by prior formation of the corresponding nitro compounds as, for example, by nitration of the phenyl compounds, followed by reduction to the amino compounds. The amino group may then be acylated to produce the acylamino compounds.

The acid group of compound 5 may be esterified by conventional methods such as initial conversion to the acid chloride with the aid of thionyl chloride followed by reaction with the desired alcohol or, alternatively, by coupling the acid with the desired alcohol in the presence of a coupling reagent such as dicyclohexylcarbodiimide to produce 6.

The amides, 7, are prepared by first converting the acids, 5, to the corresponding acid chloride with, for example, thionyl chloride, followed by reaction with the desired amine in the presence of an acid scavenger.

REACTION SEQUENCE

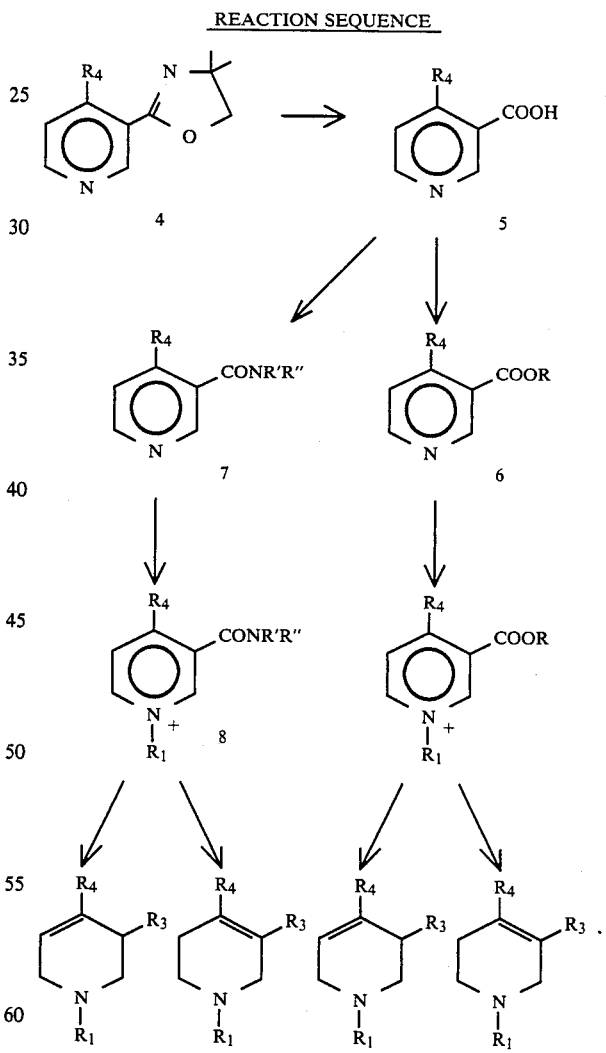

The nitrogen atom of the pyridine ring is substituted by first forming the pyridinium salt with a halogen derivative of the desired substituent to form the salts, 8 or 8A, followed by reduction with, for example, a borohydride reducing agent. This reduction affords a mixture of the 1,2,5,6-tetrahydro- and 1,2,3,6-tetrahydropyridine compounds which are separated by conventional means such as column chromatography.

The nitrogen-substituent, $R_1$, may be removed or replaced using standard methodologies such as those described by T. A. Montzka et al., *Tetrahedron Letters*, (1974), 1325-1327 and T. S. Manoharan et al., *Ind. J. Chem.*, (1984) 23B, 5-11.

Except in those cases where the basic nitrogen atom in the tetrahydropyridine ring is substituted with acyl or alkoxycarbonyl, the compounds of the present invention form pharmaceutically acceptable salts with organic and inorganic acids. Examples of suitable acids for the formation of pharmaceutically acceptable salts are hydrochloric, sulfuric, phosphoric, acetic, benzoic, citric, malonic, salicylic, malic, fumaric, succinic, tartaric, lactic, gluconic, ascorbic, maleic, benzenesulfonic, methane- and ethanesulfonic, hydroxymethane- and hydroxyethanesulfonic, aspartic, and the like.

The salts are prepared by contacting the free base form of the compounds of this invention with a sufficient amount of the desired acid to produce the salt in the conventional manner. The free base forms may be regenerated, if desired, by treating the salt form with a base. For example, dilute aqueous solutions of such bases as sodium hydroxide, potassium carbonate, ammonia, and sodium bicarbonate may be utilized for this purpose.

In the compounds of the present invention where $R_3$ is a carboxylic acid group, pharmaceutically acceptable salts may be formed with suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di- and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.* 66 (1): 1-19 (1977)).

The salts are prepared by contacting the free acid form of the compounds of this invention with a sufficient amount of the desired base to produce the salt in the conventional manner. The free acid forms may be regenerated, if desired, by treating the salt form with an acid. For example, a dilute aqueous solutions of hydrochloric acid may be utilized for this purpose.

The free acid or base forms of the compounds of this invention differ somewhat from their respective salt forms in such physical properties as melting point and solubility in polar solvents, but the salts are otherwise equivalent to their respective free acid or base forms for the purposes of the invention.

The biological activity of the compounds of the present invention was evaluated by determining the extent of binding of the compounds at the muscarinic binding site, employing the methodology of J. Ellis et al., *Brain Research*, 193: 189-198 (1980).

The compounds were assayed at one or more concentrations in each binding assay. The concentration of compound required to inhibit 50% of the specific binding was determined by a non-linear curve fit of binding data at five or more concentrations and recorded as an $IC_{50}$ value.

Binding data for several representative compounds of the present invention are presented in Table A.

TABLE A

| COMPOUND | BINDING ($IC_{50}$) |
|---|---|
| Arecoline (Prior art) | 1.1 $\mu M$ |
| Example 1 | 0.31 $\mu M$ |
| Example 2 | 3 $\mu M$ |
| Example 4 | 8 $\mu M$ |
| Example 5 | 0.58 $\mu M$ |
| Example 6 | 1 $\mu M$ |
| Example 8 | 9 $\mu M$ |
| Example 11 | 0.1 $\mu M$ |
| Example 19 | 1.56 $\mu M$ |
| Example 21 | 3.16 $\mu M$ |
| Example 22 | 6.5 $\mu M$ |
| Example 23 | 0.90 $\mu M$ |
| Example 25 | 2 $\mu M$ |
| Example 26 | 0.14 $\mu M$ |
| Example 27 | 3 $\mu M$ |
| Example 28 | 6 $\mu M$ |
| Example 33 | 5 $\mu M$ |
| Example 38 | 4 $\mu M$ |
| Example 39 | 0.4 $\mu M$ |
| Example 44 | 9 $\mu M$ |
| Example 41 | 10 $\mu M$ |
| Example 43 | 0.4 $\mu M$ |
| Example 45 | 0.3 $\mu M$ |
| Example 46 | 10 $\mu M$ |
| Example 47 | 0.6 $\mu M$ |
| Example 48 | 0.1 $\mu M$ |
| Example 52 | 5 $\mu M$ |
| Example 53 | 0.9 $\mu M$ |
| Example 55 | 5 $\mu M$ |
| Example 57 | 10 $\mu M$ |
| Example 62 | 0.26 $\mu M$ |
| Example 63 | 3.64 $\mu M$ |
| Example 64 | 10 $\mu M$ |
| Example 72 | 10 $\mu M$ |
| Example 74 | 2 $\mu M$ |
| Example 75 | 0.58 $\mu M$ |
| Example 82 | 7 $\mu M$ |
| Example 87 | 0.8 $\mu M$ |
| Example 88 | 0.36 $\mu M$ |
| Example 90 | 1 $\mu M$ |
| Example 91 | 0.1 $\mu M$ |
| Example 94 | 10 $\mu M$ |

Several representative compounds of the present invention were also assayed in an in vivo test designed to assess the ability of the compounds to reverse retrograde amnesia in rats produced by electroconvulsive shock treatment. Activity of a compound in this test is indicative of potential cognition activating activity in human patients suffering from impaired cognitive function.

In the test, groups of fifty weanling rats (Charles River CD strain) are randomly divided into five subgroups of ten rats each. The rats are trained by placing them in a highly illuminated 6 inch by 8 inch box which opens into a darkened 8 inch by 12 inch chamber having electrified grids. Initially, rats move freely from the illuminated compartment to the darkened chamber through a 4 inch by 4 inch doorway.

When a rat has all four feet within the darkened chamber, the floor of the darkened chamber is electrified and the rat is electrically shocked until it exits to the original illuminated area. If a rat reenters the darkened chamber before one minute has elapsed, it again receives a mild foot shock until it exits to the illuminated area. When the rat remains in the illuminated area for a period of one minute, it is removed and placed in a group holding cage.

Two hours after the above training, the rats are given a single 20 ma electroconvulsive shock of 1 second duration and immediately returned to the holding cage.

Two hours after the delivery of the shock, the rats are administered the test compound orally, or intraperitoneally or intramuscularly for special tests. The test compounds are generally administered at doses of 1, 10, and 100 mg/kg of body weight.

One hour after treatment with the test compound, the rats are tested for retention of the avoidance response. This is accomplished by placing a drug-treated rat in the illuminated area of the test chamber. Any rat which remains in the illuminated area and does not enter the darkened chamber for one minute is designated as having retained the avoidance response. Any rat entering the darkened chamber within sixty seconds is designated as having amnesia for this response.

In this test, the control experiments showed (1) that all rats entered the darkened chamber if no foot shock was delivered during the training period; (2) few animals which were trained for the avoidance response when retested if no electroconvulsive shock was administered between initial training and retesting; and (3) the majority of rats which had been trained and received the electroconvulsive shock but no drug treatment reentered the darkened chamber upon retesting.

The five sub-groups of ten rats each were treated as follows:

TABLE B

| Group | Treatment |
| --- | --- |
| Baseline control group | ECS*, placebo |
| Ceiling control group | No ECS, placebo |
| First dose group | ECS, test compound |
| Second dose group | ECS, test compound |
| Third dose group | ECS, test compound |

*ECS = Electroconvulsive shock treatment

A 50% difference between the baseline and ceiling control groups was required to evaluate a particular test compound. If a difference of less than 50% was observed, the results of that particular experiment were discarded.

A test compound was considered "active" (A) if the difference between the numbers of animals in the drug and control groups reentering the darkened chamber was equal or greater than three out of ten; if less than three, the test compound was considered "inactive" (N). Under the test conditions, a difference of this magnitude is statistically significant using the multinomial expansion of the statistical chi-square test. The results of these tests for several representative compounds of the present invention appear in Table C.

TABLE C

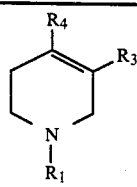

| | | | Dose (mg/kg) | | |
| --- | --- | --- | --- | --- | --- |
| $R_1$ | $R_3$ | $R_4$ | 0.01 | 0.1 | 1.0 |
| Methyl | —COOCH$_3$ | Phenyl | 57 (A) | 57 (N) | 0 (N) |
| Ethyl | —COOCH$_3$ | Phenyl | 20 (N) | 32 (N) | 20 (N) |
| Ethyl | —COOCH$_2$—phenyl | Phenyl | 40 (N) | 20 (N) | 40 (N) |
| n-Propyl | —COOCH$_3$ | Phenyl | 57 (A) | 81 (A) | 57 (A) |

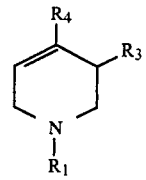

| Methyl | —COOCH$_3$ | Phenyl | 50 (A) | 17 (N) | 50 (A) |
| Ethyl | —COOCH$_3$ | Phenyl | 40 (N) | 0 (N) | 0 (N) |
| Propyl | —COOCH$_3$ | Phenyl | 62 (A) | 62 (A) | 25 (N) |

For preparing pharmaceutical compositions from the compounds of this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation in is unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

In therapeutic use as agents for treating cerebral insufficiency, the compounds utilized in the pharmaceutical method of this invention are administered to the patient at dosage levels of from 0.7 to 7000 mg per day. For a normal human adult of approximately 70 kg of body weight, this translates into a dosage of from 0.01 to 100 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

The following preparative examples are provided to enable one skilled in the art to practice the invention, and are illustrative thereof. They are not to be read as limiting the scope of the invention as it is defined by the appended claims.

The compounds listed in Tables D and E were prepared by the general synthetic methods described above. $R_1$ alkyl substituents in the cases of Example 10, 17, 65, and 93 were replaced by alkoxycarbonyl groups or hydrogen employing the methods detailed by T. A. Montkza et al., *Tetrahedron Letters*, (1974) 1325 and T. S. Manoharan et al., *Indian J. Chem.*, (1984) 23B, 5.

In the cases of Examples 12 and 68, the $R_3$ ester groups were converted to the corresponding carboxylic acid groups employing the method detailed in E. D. Langanis et al., *Tetrahedron Letters*, 25: 5831 (1984).

TABLE D

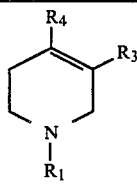

| EXAMPLE | $R_1$ | $R_3$ | $R_4$ | M.p. (SALT) |
|---|---|---|---|---|
| 1 | Ethyl | —COOCH$_2$—phenyl | Phenyl | 123–124° C. (HCl) |
| 2 | n-Propyl | —COOCH$_2$—phenyl | Phenyl | 174–175° C. (HCl) |
| 3 | Ethyl | —CONHCH$_2$—phenyl | Phenyl | 95–98° C. (HCl.H$_2$O) |
| 4 | Phenylmethyl | —COOCH$_3$ | Phenyl | 156.5–159° C. (Oxalate) |
| 5 | Ethyl | —COO—cyclopentyl | Phenyl | 118–119° C. (Oxalate) |
| 6 | —CH$_2$CH=CH$_2$ | —COOCH$_2$—phenyl | Phenyl | 155–156° C. (HCl) |
| 7 | Ethyl | —CONHCH$_3$ | Phenyl | 103–105° C. (Free base) |
| 8 | Ethyl | —CON(CH$_3$)$_2$ | Phenyl | 181–183° C. (Oxalate) |
| 9 | Propyl | —CONHOCH$_2$—phenyl | Phenyl | 143–145° C. (Free base) |
| 10 | Hydrogen | —COOCH$_3$ | Phenyl | 186.5–187° C. (HCl) |
| 11 | Ethyl | —CON(piperidinyl) | Phenyl | 227–230° C. (HCl) |
| 12 | n-Propyl | —COOH | Phenyl | 204.5–208 (Na.H$_2$O) |
| 13 | n-Propyl | —COOCH(phenyl)CH$_3$ | Phenyl | 137–140° C. (HCl.¼H$_2$O) |
| 14 | Ethyl | —CON(piperidinyl)=C(phenyl)$_2$ | Phenyl | 130–134° C. (HCl.H$_2$O) |

TABLE D-continued

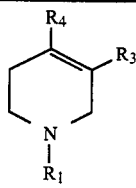

| EXAMPLE | R₁ | R₃ | R₄ | M.p. (SALT) |
|---|---|---|---|---|
| 15 | Ethyl | —CON(OCH₂CH₂CH₂) (tetrahydrooxazine) | Phenyl | 85–92° C. (HCl.1.5H₂O) |
| 16 | Cyclopentyl | —COOCH₃ | Phenyl | 170–175° C. (HCl) |
| 17 | —COOCH₂CH₃ | —COOCH₃ | Phenyl | Oil (Hemihydrate) |
| 18 | n-Propyl | —COOCH₃ | n-Butyl | 96–100° C. (Oxalate) |
| 19 | Ethyl | —COOCH₃ | 3,4-Dichlorophenyl | 141–142° C. (Oxalate) |
| 20 | Ethyl | —COOCH₃ | 2-Thienyl | 164–167° C. (HCl) |
| 21 | Methyl | —COOCH₃ | Phenyl | 96–97° C. (1.4 Oxalate) |
| 22 | n-Propyl | —COOCH₃ | Phenyl | 152–154° C. (Oxalate) |
| 23 | Ethyl | —COOCH₃ | Phenyl | 159–162° C. (Oxalate) |
| 24 | —CH₂CH₂—phenyl | —COOCH₃ | Phenyl | 195–197° C. (Oxalate) |
| 25 | Ethyl | —CON(CH₂CH₃)₂ | Phenyl | 178–180° C. (Oxalate) |
| 26 | Ethyl | —COOCH₂CH₂—phenyl | Phenyl | 134–135.5° C. (Oxalate) |
| 27 | Ethyl | —COOCH₃ | 3-Methylphenyl | 124–129° C. (Oxalate.0.5H₂O) |
| 28 | n-Propyl | —COOCH₃ | 3-Methylphenyl | 154–157° C. (Oxalate) |
| 29 | Ethyl | —COOCH₃ | 4-Acetoxyphenyl | 135–137° C. (Oxalate) |
| 30 | n-Propyl | —COOCH₃ | 4-Nitrophenyl | 150–152° C. (Oxalate.0.3H₂O) |
| 31 | Ethyl | —COOCH₃ | 4-Methoxyphenyl | 143–147° C. (Oxalate.1/6H₂O) |
| 32 | Ethyl | —COOCH₃ | 4-Nitrophenyl | 140° C. (dec.)(Oxalate.0.4H₂O) |
| 33 | Ethyl | —COOCH₃ | 4-Chlorophenyl | 154–155.5° C. (Oxalate.0.5H₂O) |
| 34 | Ethyl | —COOCH₂CH₃ | 3-Methylphenyl | 135–139° C. (Oxalate) |
| 35 | n-Butyl | —COOCH₃ | Phenyl | 149–152° C. (Oxalate) |
| 36 | Ethyl | —COOCH₃ | 4-Methylphenyl | 169.5–170.5° C. (Oxalate.0.1H₂O) |
| 37 | n-Propyl | —COOCH₃ | 4-Methylphenyl | 144–145° C. (Oxalate.0.1H₂O) |
| 38 | Ethyl | —COOCH₃ | 4-Fluorophenyl | 97–98.5° C. (1.5 Oxalate) |
| 39 | Ethyl | —COOCH(CH₃)₂ | Phenyl | 153–153.5° C. (Oxalate) |
| 40 | Diethyl (I⁻) | —COOCH₃ | Phenyl | 209–210° C. |
| 41 | n-Propyl | —CON(CH₂CH₃)₂ | Phenyl | 168° C. (dec.)(Oxalate.0.5H₂O) |
| 42 | Ethyl | —CONHCH₂CH₃ | Phenyl | 75–80° C. (Oxalate) |
| 43 | n-Propyl | —COOCH₂—phenyl | 4-Chlorophenyl | 171–172° C. (HCl) |
| 44 | Ethyl | —CONHCH(CH₃)₂ | Phenyl | 133–136° C. (HCl.H₂O) |
| 45 | Ethyl | —CONH—cyclohexyl | Phenyl | 179–180° C. (HCl.H₂O) |
| 46 | n-Propyl | —CONHCH₂—phenyl | Phenyl | 96–98° C. (Free base) |
| 47 | Ethyl | —CONH—cyclopentyl | Phenyl | 146–148° C. (HCl.H₂O) |
| 48 | Ethyl | —COO—cyclohexyl | Phenyl | 108.5–110° C. (1.4 Oxalate) |
| 49 | Methyl | —COOCH₂—phenyl | Phenyl | 148–149° C. (HCl) |
| 50 | n-Propyl | —CONHCH₃ | Phenyl | 130–132° C. (Free base) |
| 51 | n-Propyl | —CONHCH(CH₃)₂ | Phenyl | 98–99° C. (Free base) |
| 52 | Ethyl | —CONHCH₂CH₂—phenyl | Phenyl | 78–82° C. (Oxalate) |

TABLE D-continued

Structure: tetrahydropyridine with R4 at 4-position, R3 at 3-position, N-R1

| EXAMPLE | R1 | R3 | R4 | M.p. (SALT) |
|---|---|---|---|---|
| 53 | Ethyl | —CON(CH(CH3)2)2 | Phenyl | 208–210° C. (HCl) |
| 54 | n-Propyl | —CONHCH2CH3 | Phenyl | 80–83° C. (Free base) |
| 55 | n-Propyl | —CONH—cyclohexyl | Phenyl | 99–103° C. (Free base) |
| 56 | n-Butyl | —COOCH2—phenyl | Phenyl | 166–167° C. (HCl) |
| 57 | Ethyl | —CONH—phenyl | Phenyl | 118–121° C. (Free base) |
| 58 | Ethyl | —COOCH2CH2CH2—phenyl | Phenyl | 112.5–114° C. (HCl) |
| 58 | Ethyl | —COOCH3 | 2-Methoxyphenyl | 146.5–147.5° C. (HCl) |
| 59 | n-Propyl | —CONHCH2CH(phenyl)2 | Phenyl | 93° C. (HCl.1.5H2O) |
| 60 | Ethyl | —COOCH3 | [1,1-Biphenyl]-4-yl | 183.5–186° C. (HCl) |
| 61 | Methyl | —COOCH3 | Methyl | 114–116° C. (Oxalate.0.5H2O) |

TABLE E

Structure: tetrahydropyridine with R4 at 4-position, R3 at 3-position, N-R1

| EXAMPLES | R1 | R3 | R4 | M.p. (SALT) |
|---|---|---|---|---|
| 62 | Ethyl | —COOCH2—phenyl | Phenyl | 177.5–179° C. (HCl) |
| 63 | Methyl | —COOCH3 | Phenyl | 171–172° C. (Oxalate) |
| 64 | —CH2CH2—phenyl | —COOCH3 | Phenyl | 175–178° C. (Oxalate) |
| 65 | —COOCH2CH3 | —COOCH3 | Phenyl | Oil |
| 66 | Ethyl | —COOCH3 | 4-Nitrophenyl | 136–138° C. (Oxalate.1.4H2O) |
| 67 | Ethyl | —COO—cyclohexyl | Phenyl | 98–100° C. (1.25 Oxalate) |
| 68 | Ethyl | —COOH | Phenyl | 68–75° C. (HCl.0.75H2O) |
| 69 | Cyclopentyl | —COOCH3 | Phenyl | 210.5–211.5° C. (HCl) |
| 70 | Ethyl | —COOCH3 | 2-Thienyl | 166–169° C. (Oxalate) |
| 71 | n-Propyl | —COOCH3 | Phenyl | 180–181° C. (Oxalate) |
| 72 | Ethyl | —COOCH3 | Phenyl | 151–152° C. (Oxalate) |
| 73 | —CH2—phenyl | —COOCH3 | Phenyl | 180–182° C. (HCl) |
| 74 | n-Propyl | —COOCH2—phenyl | Phenyl | 100–102° C. (Oxalate) |
| 75 | Ethyl | —COOCH2CH2—phenyl | Phenyl | 188–189° C. (HCl) |
| 76 | Ethyl | —COOCH3 | 3-Methylphenyl | 152–155° C. (Oxalate.½H2O) |
| 77 | n-Propyl | —COOCH3 | 3-Methylphenyl | 162–165° C. (Oxalate.1/5H2O) |
| 78 | Ethyl | —COOCH3 | 4-Acetoxyphenyl | 148–149.5° C. (Oxalate) |
| 79 | Ethyl | —COOCH3 | 4-Methoxyphenyl | 151–154° C. (Oxalate) |
| 80 | n-Propyl | —COOCH3 | 4-Nitrophenyl | 161–163° C. (Oxalate.1/5H2O) |
| 81 | Ethyl | —COOCH3 | 4-Chlorophenyl | 164–165° C. (Oxalate.½H2O) |
| 82 | Ethyl | —COOCH2CH3 | 2-Methylphenyl | 169–170° C. (Oxalate) |
| 83 | n-Butyl | —COOCH3 | Phenyl | 171–172° C. (Oxalate) |
| 84 | Ethyl | —COOCH3 | 4-Methylphenyl | 163–164° C. (Oxalate) |
| 85 | Ethyl | —COOCH3 | 4-Fluorophenyl | 148–149° C. (Oxalate) |
| 86 | n-Propyl | —COOCH3 | 4-Methylphenyl | 166–167.5° C. (Oxalate) |

TABLE E-continued

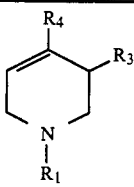

| EXAMPLES | R₁ | R₃ | R₄ | M.p. (SALT) |
|---|---|---|---|---|
| 87 | Ethyl | —COOCH(CH₃)₂ | Phenyl | 186–187° C. (Oxalate) |
| 88 | Ethyl | —COO—cyclopentyl | Phenyl | 127–128° C. (Oxalate) |
| 89 | Ethyl | —COOCH₃ | 3,4-Dichlorophenyl | 151–152° C. (Oxalate) |
| 90 | n-Propyl | —COOCH₂—phenyl | 4-Chlorophenyl | 75–76.5° C. (Free base) |
| 91 | Ethyl | —COO—cyclohexyl | Phenyl | 98–100° C. (1.25 Oxalate) |
| 92 | Methyl | —COOCH₂—phenyl | Phenyl | 174–175° C. (HCl) |
| 93 | Hydrogen | —COOCH₃ | Phenyl | 163.5–164.5 (HCl) |
| 94 | n-Butyl | —COOCH₂—phenyl | Phenyl | 185–186° C. (HCl) |
| 95 | n-Propyl | —COOCHCH₃(phenyl) | Phenyl | 140° C. (dec.)(HCl) |
| 96 | Ethyl | —COOCH₂CH₂CH₂—phenyl | Phenyl | 158.5–159.5° C. (HCl) |
| 97 | Ethyl | —COOCH₃ | 2-Methoxyphenyl | 166–166.5° C. (HCl) |
| 98 | Ethyl | —COOCH₃ | [1,1'-Biphenyl]-4-yl | 83–85° C. (Free base) |

The following illustrative synthetic examples, drawn from Tables D and E, are provided to enable one skilled in the art to practice the present invention.

EXAMPLE 3

Preparation of 1-ethyl-1,2,5,6-tetrahydro-4-phenyl-N-(phenylmethyl)-3-pyridinecarboxamide, monohydrochloride Employing the general method of Examples 45 and 41 1-ethyl-1,2,5,6-tetrahydro-4-phenyl-N-(phenylmethyl)-3-pyridinecarboxamide was prepared as the hydrochloride salt, mp 95–95° C.

The infrared spectrum of the product showed principal absorption at 1629 reciprocal centimeters.

The 200 MHz proton magnetic resonance spectrum of the product showed signals at 7.28–7.32 (multiplet, 4 protons), 7.13–7.16 (multiplet, 4 protons), 6.77–6.82 (multiplet, 2 protons), 4.06–4.17 (multiplet, 3 protons), 3.76–3.84 (multiplet, 1 proton), 3.54–3.72 (multiplet, 1 proton), 3.1503.30 (multiplet, 3 protons), 2.48 (broad singlet, 2 protons), and 1.30 (triplet, 3 protons) ppm downfield from the tetramethylsilane signal.

Analysis for $C_{29}H_{24}N_2O \cdot HCl \cdot H_2O$ Calculated: C, 67.28%; H, 7.26%; N, 7.47%; Found: C, 67.56%; H, 7.30%; N, 7.51%.

EXAMPLE 7

Preparation of 1-ethyl-1,2,5,6-tetrahydro-N-methyl-4-phenyl-3-pyridinecarboxamide Employing the general method of Example 8, 1-ethyl-1,2,5,6-tetrahydro-N-methyl-4-phenyl-3-pyridinecarboxamide, mp 103°–105° C.

The infrared spectrum of the product showed principal absorption at 1641 reciprocal centimeters.

The 100 MHz proton magnetic resonance spectrum of the product showed signals at 7.0–7.4 (multiplet, 5 protons), 3.1–3.3 (multiplet, 2 protons), 2.3–2.7 (multiplet, 9 protons), and 1.17 (triplet, 3 protons) ppm downfield from the tetramethylsilane signal.

Analysis for $C_{15}H_{20}N_2O$: Calculated: C, 73.74%; H, 8.25%; N, 11.46%; Found: C, 73.58%; H, 8.14%; N, 11.48%.

EXAMPLE 8

Preparation of 1-ethyl-1,2,5,6-tetrahydro-N,N-dimethyl-4-phenyl-3-pyridinecarboxamide, ethanedioate 4-Phenylnicotinic acid (7.07 g, 30 mmol) was suspended in 200 ml of dichloromethane and 8.4 ml (60 mmol) of triethylamine was added. The mixture was stirred until all of the acid had dissolved. Thionyl chloride (2.4 ml, 33 mmol) was added and the mixture was stirred at ambient temperature overnight. To this mixture was added 100 ml of dichloromethane saturated with dimethylamine.

After addition was complete, the mixture was stirred for 1 hour, washed twice with water, once with brine solution, dried over anhydrous magnesium sulfate, and evaporated to yield 5.74 g of N,N-dimethyl-4-phenyl-3-pyridinecarboxamide as a yellow oil which solidified upon standing.

The solid amide was dissolved in 10 ml (120 mmol) of ethyl iodide and heated under reflux overnight, and the excess ethyl iodide was removed under vacuum to give a yellow solid. This material was suspended in 200 ml of diethyl ether and stirred for one hour, filtered, and dried in vacuum to give 8.5 g of the ethylpyridinium salt.

The quaternary salt was suspended in 150 ml of absolute ethanol and 2.1 g (56 mmol) of sodium borohydride was added. This mixture was stirred at ambient temperature overnight, after which time the mixture was acidified with 1 M HCl and stirred for an additional two hours. The mixture was then neutralized with aqueous sodium bicarbonate solution, diluted with 100 ml of water, and extracted three times with dichloromethane.

The organic solutions were combined, washed with water, and then with brine solution, dried over anhydrous magnesium sulfate, and evaporated to give 5.7 g of a golden-colored oil. This oil was chromatographed on silica gel, eluting with 15% methanol in diethyl ether. The resulting purified oil was dissolved in diethyl ether and treated with an ethereal solution of oxalic acid to yield 3.7 g of 1-ethyl-1,2,5,6-tetrahydro-N,N-dimethyl-4-phenyl-3-pyridinecarboxamide, ethanedioate, mp 181°–183° C.

The infrared spectrum of the product showed principal absorption at 1632 and 1193 reciprocal centimeters.

The 100 MHz proton magnetic resonance spectrum of the product showed signals at 7.2–7.4 (multiplet, 5 protons), 3.0–3.4 (multiplet, 8 protons), 2.63 (singlet, 3 protons), 2.5 (singlet, 3 protons) and 1.27 (triplet, 3 protons) ppm downfield from the tetramethylsilane signal.

Analysis for $C_{16}H_{22}N_2O \cdot C_2O_4H_2$: Calculated: C, 62.06%; H, 6.94%; N, 8.04%; Found: C, 62.45%; H, 6.88%; N, 8.01%.

EXAMPLE 9

Preparation of 1,2,5,6-tetrahydro-4-phenyl-N-phenylmethoxy-1-propyl-3-pyridinecarboxamide Employing the general method of Example 8, 1,2,5,6-tetrahydro-4-phenyl-N-phenylmethoxy-1-propyl-3-pyridinecarboxamide, mp 143°–145° C. was prepared from O-(phenylmethyl)hydroxylamine hydrochloride, 4-phenyl-3-pyridinecarboxylic acid, and propyl iodide.

The infrared spectrum of the product showed principal absorption at 1642, 1444, 708, and 702 reciprocal centimeters.

The 100 MHz proton magnetic resonance spectrum of the product showed signals at 7.6 (broad singlet, 1 protons), 7.2 (multiplet, 10 protons), 4.8 (2 protons), 3.3 (singlet, 2 protons) 2.5 (multiplet, 6 protons), 1.5 (multiplet, 2 protons), and 0.9 (triplet, 3 protons) ppm downfield from the tetramethylsilane signal.

Analysis for $C_{22}H_{26}N_2O_2$: Calculated: C, 75.39%; H, 7.48%; N, 8.00%; Found : C, 75.00%; H, 7.30%; N, 7.91%.

EXAMPLES 10 and 93

Preparation of 1,2,5,6-tetrahydro-4-phenyl-3-pyridinecarboxylic acid, methyl ester, monohydrochloride and ($\pm$)-1,2,3,6-tetrahydro-4-phenyl-3-pyridinecarboxylic acid, methyl ester, monohydrochloride A mixture of ($\pm$)-1,2,3,6-tetrahydro-1-methyl-4-phenyl-3-pyridinecarboxylic acid, methyl ester and 1,2,5,6-tetrahydro-1-methyl-4-phenyl-3-pyridinecarboxylic acid, methyl ester was prepared by reduction of 1-methyl-4-phenyl-3-pyridinecarboxylic acid, methyl ester with sodium cyanoborohydride.

To 10.5 g of this mixture of esters was added 10.6 g of 2,2,2-trichloroethyl chloroformate and 0.62 g of potassium carbonate in 200 ml of toluene. The resulting mixture was heated at 80° C. overnight. The mixture was then cooled to room temperature, 100 ml of diethyl ether were added, and the mixture was filtered.

The filtrate was evaporated to yield 6.0 g of a yellow oil. This oil was dissolved in 500 ml of methanol, 6.0 g of zinc dust were added, and the mixture was heated under reflux for one hour. The mixture was cooled, made basic with aqueous sodium carbonate solution, and extracted three times with chloroform. The combined extracts were dried and evaporated to yield 11.0 g of crude product. Purification of this crude material by chromatography yielded two oils.

The oils were separately taken up in 450-ml portions of diethyl ether and treated with HCl-saturated 2-propanol solution until salt formation was complete. Each mixture was filtered and the solids rinsed with diethyl ether.

1,2,5,6-tetrahydro-4-phenyl-3-pyridinecarboxylic acid, methyl ester was obtained as the monohydrochloride, mp 186.5°–187° C.

The infrared spectrum of the product showed principal absorption at 1705, 1278, 753, and 707 reciprocal centimeters.

The 200 MHz proton magnetic resonance spectrum of the product showed signals at 9.82 (broad singlet, 2 protons), 7.2 (multiplet, 5 protons), and 3.40 (singlet, 3 protons) ppm downfield from the tetramethylsilane signal.

Analysis for $C_{13}H_{15}NO_2$: Calculated: C, 61.54%; H, 6.36%; N, 5.52%; Found: C, 61.84%; H, 6.68%; N, 5.31%.

($\pm$)-1,2,3,6-tetrahydro-4-phenyl-3-pyridinecarboxylic acid, methyl ester was obtained as the monohydrochloride, mp 163.5–164.5.

The infrared spectrum of the product showed principal absorption at 1734 reciprocal centimeters.

The 200 MHz proton magnetic resonance spectrum of the product showed signals at 7.3 (multiplet, 5 protons), 6.17 (singlet, 1 proton) and 3.48 (singlet, 3 protons) ppm downfield from the tetramethylsilane signal.

Analysis for $C_{13}H_{15}NO_2$: Calculated: C, 61.54%; H, 6.36%; N, 5.52%; Found: C, 61.78%; H, 6.54%; N, 5.39%.

EXAMPLE 11

Preparation of 1-[(1-ethyl-1,2,5,6-tetrahydro-4-phenyl-3-pyridinyl)carbonyl]-piperidine, monohydrochloride Employing the general method of Example 8, 1-[(1-ethyl-1,2,5,6-tetrahydro-4-phenyl-3-pyridinyl)carbonyl]piperidine, monohydrochloride, mp 227°–230° C. was prepared.

The infrared spectrum of the product showed principal absorption at 1612 reciprocal centimeters.

The 200 MHz proton magnetic resonance spectrum of the product showed signals at 7.29–7.34 (multiplet, 5 protons), 2.8–3.76 (multiplet, 12 protons), 1.28 (triplet, 3 protons), and 1.06–1.32 (multiplet, 6 protons) ppm downfield from the tetramethylsilane signal.

Analysis for $C_{19}H_{26}N_2O \cdot HCl$: Calculated: C, 68.14%; H, 8.13%; N, 8.36%; Found: C, 68.27%; H, 8.13%; N, 8.31%.

EXAMPLES 19 and 89

Preparation of 4-(3,4-dichlorophenyl)-1-ethyl-1,2,5,6-tetrahydro-3-pyridinecarboxylic acid, methyl ester, ethanedioate and 4-(3,4-dichlorophenyl)-1-ethyl-(±)-1,2,3,6-tetrahydro-3-pyridinecarboxylic acid, methyl ester, ethanedioate A suspension of 12.3 g of 4-(3,4-dichlorophenyl)-3-pyridinecarboxylic acid hydrochloride and approximately 125 ml of thionyl chloride in 4 ml of dimethylformamide was heated with stirring to a temperature just short of the boiling point. The mixture was then stirred at ambient temperature overnight while being protected from moisture.

The excess thionyl chloride was removed to leave an off-white solid residue. This material was cooled in an ice-bath, and excess methanol was added. After the exothermic reaction had subsided, the mixture was briefly heated to boiling. The mixture was cooled to ambient temperature and stirred for 15 minutes and then neutralized with aqueous sodium bicarbonate solution. This mixture was extracted three times with dichloromethane. The combined organic extracts were dried and evaporated to yield 13.6 g of a light-brown solid which was purified by chromatography to yield 10.3 g of a white solid.

This material (9.7 g) was mixed with 10 ml of ethyl iodide and 40 ml of acetonitrile, and the mixture was stirred at 45° C. overnight. After cooling the mixture to ambient temperature, diethyl ether was added until the mixture became cloudy. Upon further stirring at ambient temperature, the pyridinium salt crystallized from solution. Diethyl ether (150 ml) was further added, and the mixture was stirred vigorously for one hour. The solid was separated by filtration, rinsed twice with diethyl ether, and air-dried to yield 10.7 g of the pyridinium salt.

The quaternary salt (10.5 g) was dissolved in 200 ml of methanol and to this stirred solution was added 3.0 g of sodium cyanoborohydride. After one hour, 100 ml of 1 M HCl was added dropwise, and after addition was complete, the mixture was stirred at ambient temperature overnight. The mixture was then neutralized with aqueous sodium bicarbonate solution, and then extracted four times with dischloromethane.

The combined organic extracts were washed with 200 ml of 1 M NaOH, dried and evaporated to yield a yellow oil which slowly solidified upon standing.

This oil was purified by chromatographic methods to yield two products. These products were separately dissolved in diethyl ether and treated with an excess of an ethereal solution of oxalic acid. The white solids which formed in each case were filtered, rinsed twice with diethyl ether, and air dried. The salts were pulverized and dessicated under vacuum overnight.

4-(3,4-Dichlorophenyl)-1-ethyl-1,2,5,6-tetrahydro-3-pyridinecarboxylic acid, methyl ester, was obtained as the ethanedioate salt, mp 141°–142° C.

The infrared spectrum of the product showed principal absorption at 1729 and 1713 reciprocal centimeters.

The 200 MHz proton magnetic resonance spectrum of the product showed signals at 7.4 (multiplet, 3 protons), 3.49 (singlet, 3 protons), 3.09 (quartet, 2 protons), and 1.24 (triplet, 3 protons) ppm downfield from the tetramethylsilane signal.

Analysis for $C_{15}H_{17}NO_2Cl_2 \cdot C_2H_2O_2$: Calculated: C, 50.51%; H, 4.74%; N, 3.46%; Found: C, 50.48%; H, 4.93%; N, 3.44%.

(±)-4-(3,4-Dichlorophenyl)-1-ethyl-1,2,3,6-tetrahydro-3-pyridinecarboxylic acid, methyl ester was obtained as the ethanedioate salt, mp 151°–152° C.

The infrared spectrum of the product showed principal absorption at 1742 reciprocal centimeters.

The 200 MHz proton magnetic resonance spectrum of the product showed signals at 7.5 (multiplet, 3 protons), 6.29 (doublet, 1 proton), 3.50 (singlet, 3 protons), 2.83 (quartet, 2 protons) and 1.12 (triplet, 3 protons) ppm downfield from the tetramethylsilane signal.

Analysis for $C_{15}H_{17}NO_2Cl_2 \cdot C_2H_2O_2$: Calculated: C, 50.51%; H, 4.74%; N, 3.46%; Found: C, 50.22%; H, 4.62%; N, 3.39%.

EXAMPLE 41

Preparation of N,N-diethyl-4-phenyl-1-propyl-1,2,5,6-tetrahydro-3-pyridinecarboxamide, ethanedioate (A) Preparation of N,N-diethyl-4-phenyl-3-pyridinecarboxamide To a mixture of diethylnicotinamide (3.56 g, 0.02 mol) and copper(I) iodide (3.8 g, 0.02 mol) in 50 ml of tetrahydrofuran was added 3.12 g (0.02 mol) of phenylchloroformate at −20° C. After addition was complete, the mixture was stirred at −20° C. for 15 minutes. Phenylmagnesium bromide (6-9 ml of a 2.9 M solution in diethyl ether) was added to the reaction mixture in a dropwise manner. This mixture was stirred at ambient temperature overnight, and then quenched with a 20% aqueous ammonium chloride solution. Diethyl ether was added, and the organic layer was separated, washed successively with 20% aquous solution of 1:1 ammonium chloride/ammonia solution, water, 10% aqueous HCl, again with water, and finally with brine solution. The organic solution was then dried and evaporated to yield 3-[(diethylamino)carbonyl]-1(4H)-pyridinecarboxylic acid, phenyl ester as a yellow oil.

Without further purification, this material was suspended in 50 ml of decalin, and 0.7 g, 0.022 mol) of sulfur was added. This mixture was heated under reflux for three hours and then cooled. Diethyl ether was added, and the mixture was extracted with 10% aqueous HCl. The acidic layer was made basic by the addition of solid potassium carbonate, and then extracted with dichloromethane. The organic extract was dried and concentrated to give 3.18 g N,N-diethyl-4-phenyl-3-pyridinecarboxamide as an oil.

(B) Preparation of N,N-diethyl-4-phenyl-1-propyl-1,2,5,6-tetrahydro-3-pyridinecarboxamide A solution of 3.18 g (0.013 mol of N,N-diethyl-4-phenyl-3-pyridinecarboxamide and 6.63 g (0.039 mol) of 1-iodopropane in 50 ml of acetonitrile was stirred and heated at 65° C. for 16 hours under a nitrogen atmosphere. Evaporation of the solvent yielded 5.07 g of the pyridinium salt as an oil which solidified to a foam under high vacuum.

The quaternary salt was dissolved in 50 ml of ethanol to which 1.13 g (0.03 mol) of sodium borohydride was added and the mixture was stirred at ambienbt temperature for 16 hours. After this time the mixture was acidified with 100 ml of 1 M HCl and 1.5 g (0.024 mol) of sodium cyanoborohydride was added. This mixture was stirred at ambient temperature for 3 hours and then made basic by the addition of solid potassium carbonate.

The basic mixture was extracted with dichloromethane, the organic layer separated and dried, and the solvent removed to yield 3.89 g of a mixture, believed to be the 4- and 6-phenyl regioisomers.

The major product was isolated by chromatography and converted to the oxalate salt to yield 1.82 g of N,N-diethyl-4-phenyl-1-propyl-1,2,5,6-tetrahydro-3-pyridinecarboxamide, ethanedioate, mp 165° C. (dec.).

The infrared spectrum of the product showed principal absorption at 1619 and 1444 reciprocal centimeters.

The 200 MHz proton magnetic resonance spectrum of the product showed signals at 1.0 (multiplet, 9 protons), 1.7 (multiplet, 2 protons), 2.5–4.0 (multiplet, 12 protons), and 7.5 (singlet, 5 protons) ppm downfield from the tetramethylsilane signal.

Analysis for $C_{19}H_{28}N_2O \cdot C_2H_2O_2$: Calculated: C, 63.13%; H, 7.82%; N, 7.01%; Found: C, 63.29%; H, 7.25%; N, 7.06%.

EXAMPLE 42

Preparation of N,1-diethyl-1,2,5,6-tetrahydro-4-phenyl-3-pyridinecarboxamide, ethanedioate Employing the general method of Example 8, N,1-diethyl-1,2,5,6-tetrahydro-4-phenyl-3-pyridinecarboxamide was prepared as the ethanedioate salt, mp 75°–80° C.

The infrared spectrum of the product showed principal absorption at 1633 reciprocal centimeters.

The 100 MHz proton magnetic resonance spectrum of the product showed signals at 7.1–7.5 (multiplet, 5 protons), 2.3–3.4 (multiplet, 3 protons), 1.23 (triplet, 3 protons), and 0.73 (triplet, 3 protons) ppm downfield from the tetramethylsilane signal.

Analysis for $C_{18}H_{24}N_2O_5$: Calculated: C, 62.06%; H, 6.94%; N, 8.04%; Found: C, 62.73%; H, 7.23%; N, 8.00%.

EXAMPLES 43 and 90

Preparation of 4-(4-chlorophenyl)-1,2,5,6-tetrahydro-1-propyl-3-pyridinecarboxylic acid, phenylmethyl ester, monohydrochloride and (±)-4-(4-chlorophenyl)-1,2,3,6-tetrahydro-1-propyl-3-pyridinecarboxylic acid, phenylmethyl ester Employing the general method of Examples 19 and 89, 4-(4-chlorophenyl)-1,2,5,6-tetrahydro-1-propyl-3-pyridinecarboxylic acid, phenylmethyl ester was prepared as the hydrochloride salt, mp 171°–172° C.

The infrared spectrum of the product showed principal absorption at 1715 reciprocal centimeters.

The 200 MHz proton magnetic resonance spectrum of the product showed signals at 7.13 (multiplet, 9 protons), 4.90 (multiplet, 2 protons), 1.77 (quartet, 2 protons), and 0.91 (triplet, 3 protons) ppm downfield from the tetramethylsilane signal.

Analysis for $C_{22}H_{24}NO_2Cl \cdot HCl$: Calculated: C, 65.03%; H, 6.20%; N, 3.45%; Found: C, 65.13%; H, 6.32%; N, 3.48%.

4-(4-Chlorophenyl)-1,2,3,6-tetrahydro-1-propyl-3-pyridinecarboxylic acid, phenylmethyl ester was obtained, mp 75°–76.5° C.

The infrared spectrum of the product showed principal absorption at 1724 reciprocal centimeters.

The 100 MHz proton magnetic resonance spectrum of the product showed signals at 7.1 (multiplet, 9 protons), 6.2 (triplet, 1 proton), 5.0 (doublet of doublets, 2 protons), and 0.9 (triplet, 3 protons) ppm downfield from the tetramethylsilane signal.

Analysis for $C_{22}H_{24}NO_2Cl$: Calculated: C, 71.44%; H, 6.54%; N, 3.79%; Found: C, 71.72%; H, 6.58%; N, 3.84%.

EXAMPLE 44

Preparation of 1-ethyl-1,2,5,6-tetrahydro-N-(1-methylethyl)-4-phenyl-3-pyridinecarboxamide, monohydrochloride Employing the general method of Example 8, 1-ethyl-1,2,5,6-tetrahydro-N-(1-methylethyl)-4-phenyl-3-pyridinecarboxamide was obtained as the monohydrochloride salt, mp 133°–136° C.

The infrared spectrum of the product showed principal absorption at 1621 and 1569 reciprocal centimeters.

The 200 MHz proton magnetic resonance spectrum of the product showed signals at 7.24–7.40 (multiplet, 5 protons), 3.05–3.37 (multiplet, 4 protons), 2.50–2.52 (multiplet, 1 proton), 1.29–1.36 (triplet, 3 protons), 0.81–0.91 (doublet, 3 protons), and 0.65–0.68 (doublet, 3 protons) ppm downfield from the tetramethylsilane signal.

Analysis for $C_{17}H_{24}N_2O \cdot HCl \cdot H_2O$: Calculated: C, 62.47%; H, 8.33%; N, 8.20%; $H_2O$, 5.51% Found: C, 62.74%; H, 8.31%; N, 8.57%; $H_2O$, 6.07%.

EXAMPLE 45

Preparation of N-cyclohexyl-1-ethyl-1,2,5,6-tetrahydro-4-phenyl-3-pyridinecarboxamide, monohydrochloride 4-Phenylnicotinic acid hydrochloride (7.07 g, 30 mmol) was suspended in 200 ml of dichloromethane and 8.4 ml (60 mmol) of triethylamine was added. The mixture was stirred until all of the acid had dissolved, and 2.4 ml of thionyl chloride (33 mmol) were added. This mixture was stirred at ambient temperature overnight. A mixture of cyclohexylamine (3.8 ml, 33 mmol), 4.2 ml (30 mmol) of triethylamine, and 50 ml of dichloromethane was added, after which the resulting mixture was heated under reflux overnight.

The reaction mixture was cooled, washed twice with water, once with brine solution, and dried over anhydrous magnesium sulfate. Evaporation of the solvent yielded a brown oil which was purified by chromatographic methods to produce 4 g of N-cyclohexyl-4-phenyl-3-pyridinecarboxamide as a glassy yellow solid.

Employing the N-alkylation and subsequent reduction methods desrcibed in Example 41, N-cyclohexyl-1-ethyl-1,2,5,6-tetrahydro-4-phenyl-3-pyridinecarboxamide was obtained as the monohydrochloride salt, mp 179°–180° C.

The infrared spectrum of the product showed principal absorption at 1620 and 1562 reciprocal centimeters.

The 200 MHz proton magnetic resonance spectrum of the product showed signals at 7.27–7.40 (multiplet, 5 protons), 3.06–4.13 (multiplet, 7 protons), 2.77 (broad singlet, 2 protons), 0.67–1.59 (multiplet, 10 protons), and 1.32 (triplet, 3 protons), ppm downfield from the tetramethylsilane signal.

Analysis for $C_{20}H_{28}N_2O \cdot HCl \cdot H_2O$: Calculated: C, 66.47%; H, 8.52%; N, 7.63%; $H_2O$, 4.91%; Found: C, 66.17%; H, 8.85%; N, 7.47%; $H_2O$, 4.86%.

EXAMPLE 46

Preparation of
1,2,5,6-tetrahydro-4-phenyl-N-phenylmethyl-1-propyl-3-pyridinecarboxamide (A) Preparation of 4-phenyl-N-phenylmethyl-3-pyridinecarboxamide To a solution of 2.35 g (0.01 mol) of 4-phenylnicotinic acid hydrochloride and 2.8 ml (0.02 mol) of triethylamine in 50 ml of dichloromethane was added 1.30 g (0.01 mol) of thionyl chloride in 10 ml of dichloromethane in a dropwise manner. This mixture was stirred at ambient temperature overnight, after which a solution of 1.07 g (0.01 mol) of benzylamine and 2.0 ml of triethylamine in 10 ml of dichloromethane was added in a dropwise manner. This mixture was stirred for 3 hours, then washed with water, aqueous sodium carbonate solution, and again with water. The organic layer was separated, dried, and evaporated to yield 3.57 g of a solid residue. This residue was taken up in pentane, stirred vigorously, and the solid collected by filtration to yield 2.36 g of crude N-phenylmethyl-4-phenyl-3-pyridinecarboxamide. After purification by chromatographic techniques, this material exhibited a melting point of 164°–166° C.

(B) Preparation of 1,2,5,6-tetrahydro-4-phenyl-N-phenylmethyl-1-propyl-3-pyridinecarboxamide A mixture of 7.00 g (0.024 mol) of N-benzyl-4-phenyl-3-pyridinecarboxamide and 4.08 g (0.024 mol) of 1-iodopropane was stirred at 60° C. for 16 hours. Additional iodopropane (10 ml) was added, and the resulting mixture stirred an additional 16 hours at 80° C. The solvent was removed and the resulting yellow solid washed with diethyl ether to give 11.24 g of the pyridinium salt.

A suspension of the quaternary salt in 100 ml of ethanol was treated with 2.72 g (0.024 mol) of sodium borohydride. The resulting clear solution was stirred at ambient temperature for 16 hours, and then acidified with 200 ml of 1 M HCl. After further stirring for two hours at room temperature, the solution was made basic by the addition of solid potassium carbonate and then extracted with dichloromethane. The organic layer was dried and evaporated to give 7.72 g of crude product.

Purification of the crude product by chromatographic methods gave pure 1,2,5,6-tetrahydro-4-phenyl-N-phenylmethyl-1-propyl-3-pyridinecarboxamide, mp 96°–98° C.

The infrared spectrum of the product showed principal absorption at 3309, 2953, 1649, 1544, 1456, and 701 reciprocal centimeters.

The proton magnetic resonance spectrum of the product showed signals at 1.0 (triplet, 3 protons), 1.5 (multiplet, 2 protons), 2.3–2.8 (broad multiplet, 6 protons), 3.3 (singlet, 2 protons), 4.2 (doublet, 2 protons), 5.2 (broad singlet, 1 proton), and 7.2 (multiplet, 9 protons) ppm downfield from the tetramethylsilane signal.

Analysis for $C_{22}H_{26}N_2O$: Calculated: C, 79.00%; H, 7.84%; N, 8.38%; Found: C, 79.31%; H, 8.15%; N, 8.38%.

EXAMPLE 47

Preparation of
N-cyclopentyl-1-ethyl-1,2,5,6-tetrahydro-4-phenyl-3-pyridinecarboxamide, monohydrochloride Employing the general method of Example 8, N-cyclopentyl-1-ethyl-1,2,5,6-tetrahydro-4-phenyl-3-pyridinecarboxamide was prepared as the monohydrochloride salt, mp 146°–148° C.

The infrared spectrum of the product showed principal absorption at 1620 and 1568 reciprocal centimeters.

The 200 MHz proton magnetic resonance spectrum of the product showed signals at 7.23–7.43 (multiplet, 5 protons), 3.53–4.08 (multiplet, 3 protons), 3.06–3.33 (multiplet, 4 protons), 2.74 (broad singlet, 2 protons), 0.86–1.58 (multiplet, 8 protons), and 1.28 (triplet, 3 protons) ppm downfield from the tetramethylsilane signal.

Analysis for $C_{19}H_{26}N_2O \cdot HCl \cdot H_2O$: Calculated: C, 64.67%; H, 8.00%; N, 7.94%; $H_2O$, 5.10%; Found: C, 64.36%; H, 7.98%; N, 8.07%; $H_2O$, 5.28%.

EXAMPLES 48 and 67

Preparation of
1-ethyl-1,2,5,6-tetrahydro-4-phenyl-3-pyridinecarboxylic acid, cyclohexyl ester, ethanedioate and
(±)-1-ethyl-1,2,3,6-tetrahydro-4-phenyl-3-pyridinecarboxylic acid, cyclohexyl ester, ethanedioate Employing the general method of Examples 19 and 89, 1-ethyl-1,2,5,6-tetrahydro-4-phenyl-3-pyridinecarboxylic acid, cyclohexyl ester was prepared as the ethanedioatesalt, mp 108.5°–110° C.

The infrared spectrum of the product showed principal absorption at 1736, 1699, and 701 reciprocal centimeters.

The 200 MHz proton magnetic resonance spectrum of the product showed signals at 7.2 (multiplet, 5 protons), 4.50 (multiplet, 1 proton), 3.19 (quartet, 2 protons), and 1.1 multiplet, 13 protons) ppm downfield from the tetramethylsilane signal.

Analysis for $C_{20}H_{27}NO_2 \cdot 1.4 \, C_2H_2O_2$: Calculated: C, 62.31%; H, 6.83%; N, 3.12%; Found: C, 62.18%; H, 6.89%; N, 3.10%.

(±)-1-Ethyl-1,2,3,6-tetrahydro-4-phenyl-3-pyridinecarboxylic acid, cyclohexyl ester was prepared as the ethanedioate salt, mp 98°–100° C.

The infrared spectrum of the product showed principal absorption at 1731, 1637, and 696 reciprocal centimeters.

The 200 MHz proton magnetic resonance spectrum of the product showed signals at 7.3 (multiplet, 5 protons), 6.12 (doublet, 1 proton), 3.00 (quartet, 2 protons), and 1.3 multiplet, 13 protons) ppm downfield from the tetra- methylsilane signal.

Analysis for $C_{20}H_{27}NO_2 \cdot 1.25 \, C_2H_2O_2$: Calculated: C, 63.44%; H, 6.98%; N, 3.29%; Found: C, 63.31%; H, 6.89%; N, 3.11%.

EXAMPLE 49 and 92

Preparation of
1,2,5,6-tetrahydro-1-methyl-4-phenyl-3-pyridinecarboxylic acid, phenylmethyl ester, monohydrochloride
and
(±)-1,2,3,6-tetrahydro-1-methyl-4-phenyl-3-pyridinecarboxylic acid, phenylmethyl ester, monohydrochloride Employing the general method of Example 19 and 89, 1,2,5,6-tetrahydro-1-methyl-4-phenyl-3-pyridinecarboxylic acid, phenylmethyl ester was prepared as the monohydrochloride, mp 149°–149° C.

The infrared spectrum of the product showed principal absorption at 1706 and 701 reciprocal centimeters.

The 200 MHz proton magnetic resonance spectrum of the product showed signals at 11.47 (broad, 1 proton), 7.1 (multiplet, 10 protons), 4.94 (singlet, 2 protons), and 2.90 (singlet, 3 protons) ppm downfield from the tetramethylsilane signal.

Analysis for $C_{20}H_{21}NO_2.HCl$: Calculated: C, 69.86%; H, 6.45%; N, 4.07%; Found: C, 69.51%; H, 6.47%; N, 3.96%.

(±)-1,2,3,6-Tetrahydro-1-methyl-4-phenyl-3-pyridinecarboxylic acid, phenylmethyl ester was prepared as the monohydrochloride, mp 174°–175° C.

The infrared spectrum of the product showed principal absorption at 1737 and 698 reciprocal centimeters.

The 200 MHz proton magnetic resonance spectrum of the product showed signals at 11.7 (broad, ½ proton), 10.27 (broad, ½ proton), 7.1 (multiplet, 10 protons), 6.19 (singlet, 1 proton), 5.00 (singlet, 2 protons), and 2.89 (singlet, 3 protons) ppm downfield from the tetramethylsilane signal.

Analysis for $C_{20}H_{21}NO_2.HCl$: Calculated: C, 69.86%; H, 6.45%; N, 4.07%; Found: C, 69.54%; H, 6.51%; N, 4.07%.

EXAMPLE 51

Preparation of
1,2,5,6-tetrahydro-N-methylethyl-4-phenyl-1-propyl-3-pyridinecarboxamide Employing the general method of Examples 45 and 41, 1,2,5,6-tetrahydro-N-methylethyl-4-phenyl-1-propyl-3-pyridinecarboxamide, mp 98°–99° C. was prepared.

The infrared spectrum of the product showed principal absorption at 3308, 2937, 1619, 1541, 1466, and 704 reciprocal centimeters.

The 200 MHz proton magnetic resonance spectrum of the product showed signals at 0.8 (doublet, 3 protons), 1.0 (multiplet, 5 protons), 1.9 (multiplet, 2 protons), 3.0 (multiplet, 4 protons), and 3.5–4.4 (multiplet, 4 protons) ppm downfield from the tetramethylsilane signal.

Analysis for $C_{18}H_{26}N_2O$: Calculated: C, 75.48%; H, 9.15%; N, 9.78%; Found: C, 75.60%; H, 9.18%; N, 9.80%.

EXAMPLE 52

Preparation of
1-ethyl-1,2,5,6-tetrahydro-4-phenyl-N-(2-phenylethyl)-3-pyridinecarboxamide, ethanedioate Employing the general method of Example 8, 1-ethyl-1,2,5,6-tetrahydro-4-phenyl-N-(2-phenylethyl)-3-pyridinecarboxamide was prepared as the ethanedioate salt, mp 78°–82° C.

The infrared spectrum of the product showed principal absorption at 1637 and 1590 reciprocal centimeters.

The 200 MHz proton magnetic resonance spectrum of the product showed signals at 6.96–7.39 (multiplet, 10 protons), 3.72 (broad singlet, 2 protons), 3.02–3.24 (multiplet, 4 protons), 2.66 (broad singlet, 2 protons), and 2.36 (triplet, 2 protons) ppm downfield from the tetramethylsilane signal.

Analysis for $C_{22}H_{26}N_2O.C_2H_2O_2$: Calculated: C, 67.91%; H, 6.65%; N, 6.60%; Found: C, 67.63%; H, 6.88%; N, 6.39%.

EXAMPLE 53

Preparation of
1-ethyl-1,2,5,6-tetrahydro-N,N-bis(1-methylethyl)-4-phenyl-3-pyridinecarboxamide, monohydrochloride Employing the general method of Example 8, 1-ethyl-1,2,5,6-tetrahydro-N,N-bis(1-methylethyl)-4-phenyl-3-pyridinecarboxamide was prepared as the monohydrochloride salt, mp 208°–210° C.

The infrared spectrum of the product showed principal absorption at 1615 and 1445 reciprocal centimeters.

The 200 MHz proton magnetic resonance spectrum of the product showed signals at 7.34–7.45 (multiplet, 5 protons), 3.44–4.16 (multiplet, 4 protons), 2.99–3.37 (multiplet, 5 protons), 2.35–2.43 (multiplet, 1 proton), 1.33 (doublet, 6 protons), and 1.13 (triplet, 3 protons) ppm downfield from the tetramethylsilane signal.

Analysis for $C_{20}H_{30}N_2O.HCl$: Calculated: C, 68.45%; H, 8.90%; N, 7.89%; Found: C, 68.60%; H, 8.95%; N, 8.14%.

EXAMPLE 54

Preparation of
N-ethyl-1,2,5,6-tetrahydro-4-phenyl-1-propyl-3-pyridinecarboxamide Employing the general method of Examples 45 and 41, N-ethyl-1,2,5,6-tetrahydro-4-phenyl-1-propyl-3-pyridinecarboxamide, mp 80°–83° C. was prepared.

The infrared spectrum of the product showed principal absorption at 1666, 1635, 1601, 1492, 1472, and 705 reciprocal centimeters.

The 200 MHz proton magnetic resonance spectrum of the product showed signals at 0.8 (triplet, 3 protons), 1.0 (triplet, 3 protons), 1.6 (multiplet, 2 protons), 2.3–2.8 (multiplet, 6 protons), 3.0 (multiplet, 2 protons), 3.3 (singlet, 3 protons), 4.9 (broad, 1 proton), and 7.3 (multiplet, 5 protons) ppm downfield from the tetramethylsilane signal.

Analysis for $C_{17}H_{24}N_2O$: Calculated: C, 74.96%; H, 8.88%; N, 10.29%; Found: C, 74.66%; H, 8.92%; N, 10.34%.

EXAMPLES 56 and 94

Preparation of
1-butyl-1,2,5,6-tetrahydro-4-phenyl-3-pyridinecarboxylic acid, phenylmethyl ester, monohydrochloride and (±)-1-butyl-1,2,3,6-tetrahydro-4-phenyl-3-pyridinecarboxylic acid, phenylmethyl ester, monohydrochloride Employing the general method of Examples 19 and 89, 1-butyl-1,2,5,6-tetrahydro-4-phenyl-3-pyridinecarboxylic acid, phenylmethyl ester was prepared as the monohydrochloride salt, mp 166°–167° C.

The infrared spectrum of the product showed principal absorption at 1710 and 697 reciprocal centimeters.

The 200 MHz proton magnetic resonance spectrum of the product showed signals at 11.41 (broad, 1 proton), 7.1 (multiplet, 10 protons), 4.90 (singlet, 2 protons), 1.74 (multiplet, 2 protons), 1.32 (multiplet, 2 protons), and 0.90 (triplet, 3 protons) ppm downfield from the tetramethylsilane signal.

Analysis for $C_{23}H_{27}NO_2.HCl$: Calculated: C, 71.58%; H, 7.31%; N, 3.63%; Found: C, 71.82%; H, 7.29%; N, 3.66%.

(±)-1-Butyl-1,2,3,6-tetrahydro-4-phenyl-3-pyridinecarboxylic acid, phenylmethyl ester was prepared as the monohydrochloride salt. mp 185°–186° C.

The infrared spectrum of the product showed principal absorption at 1727 and 696 reciprocal centimeters.

The 200 MHz proton magnetic resonance spectrum of the product showed signals at 7.2 (multiplet, 10 protons), 6.13 (singlet, 1 proton), 5.94 (singlet, 2 protons), 2.95 (quartet, 2 protons), and 0.88 (triplet, 3 protons) ppm downfield from the tetramethylsilane signal.

Analysis for $C_{23}H_{27}NO_2 \cdot HCl$: Calculated: C, 71.58%; H, 7.31%; N, 3.63%; Found: C, 71.63%; H, 7.54%; N, 3.57%.

We claim:

1. A compound having the structural formula

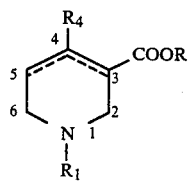

wherein the dashed lines indicate the presence of only one carbon-carbon double bond between either carbon atoms 3 and 4 or carbon atoms 4 and 5;

$R_1$ is
hydrogen;
alkyl of from one to six carbon atoms;
alkenyl of from from two to six carbon atoms;
cycloalkyl of from four to eight carbon atoms;

R is
hydrogen;
alkyl of from one to six carbon atoms;
alkenyl of from two to six carbon atoms;
cycloakly of from three to eight carbon atoms;
phenyl;
phenyl substituted with halogen, hydroxy, nitro, amino, alkyl of from one to four carbon atoms, alkyloxy of from one to four carbon atoms, or alkanoylamino of from two to six carbon atoms;

$R_4$ is
phenyl;
phenyl substituted with halogen, hydroxy, nitro, amino, alkyl of from one to four carbon atoms, alkyloxy of from one to four carbon atoms, or alkanoylamino of from two to six carbon atoms;
phenylalkyl wherein the alkyl portion contains from one to four carbon atoms, and the phenyl ring is unsubstituted or is substituted with halogen, hydroxy, alkyl of from one to four carbon atoms, or alkyloxy of from one to four carbon atoms; or a pharmaceutically acceptable salt thereof.

2. A compound in accordance with claim 1 wherein $R_1$ is alkyl of from one to six carbon atoms; $R_3$ is —COO—alkyl wherein alkyl has from one to six carbon atoms; and $R_4$ is phenyl.

3. A compound as defined in claim 1 having the name 1-ethyl-1,2,5,6-tetrahydro-4-phenyl-3-pyridinecarboxylic acid, phenylmethyl ester, or a pharmaceutically acceptable salt thereof.

4. A compound as defined in claim 1 having the name 1,2,5,6-tetrahydro-4-phenyl-1-propyl-3-pyridinecarboxylic acid, phenylmethyl ester or a pharmaceutically acceptable salt thereof.

5. A compound as defined in claim 1 having the name 1,2,5,6-Tetrahydro-4-phenyl-1-(phenylmethyl)-3-pyridinecarboxylic acid, methyl ester or a pharmaceutically acceptable salt thereof.

6. A compound as defined in claim 1 having the name 1-ethyl-1,2,5,6-tetrahydro-4-phenyl-3-pyridinecarboxylic acid, cyclopentyl ester or a pharmaceutically acceptable salt thereof.

7. A compound as defined in claim 1 having the name 1,2,5,6-tetrahydro-4-phenyl-1-(2-propenyl)-3-piperidinecarboxylic acid, phenylmethyl ester or a pharmaceutically acceptable salt thereof.

8. A compound as defined in claim 1 having the name 1,2,5,6-tetrahydro-4-phenyl-3-pyridinecarboxylic acid, methyl ester or a pharmaceutically acceptable salt thereof.

9. A compound as defined in claim 1 having the name 1,2,5,6-tetrahydro-4-phenyl-1-propyl-3-pyridinecarboxylic acid or a pharmaceutically acceptable salt thereof.

10. A compound as defined in claim 1 having the name 1,2,5,6-tetrahydro-4-phenyl-1-propyl-3-pyridinecarboxylic acid, 1-phenylethyl ester or a pharmaceutically acceptable salt thereof.

11. A compound as defined in claim 1 having the name 1-cyclopentyl-1,2,5,6-tetrahydro-4-phenyl-3-pyridinecarboxylic acid, methyl ester or a pharmaceutically acceptable salt thereof.

12. A compound as defined in claim 1 having the name 4-(3,4-dichlorophenyl)-1-ethyl-1,2,5,6-tetrahydro-3-pyridinecarboxylic acid, methyl ester of a pharmaceutically acceptable salt thereof.

13. A compound as defined in claim 1 having the name (±)-1-ethyl-1,2,3,6-tetrahydro-4-phenyl-3-pyridinecarboxylic acid, phenylmethyl ester or a pharmaceutically acceptable salt thereof.

14. A compound as defined in claim 1 having the name (±)-1,2,3,6-tetrahydro-1-methyl-4-phenyl-3-pyridinecarboxylic acid, methyl ester or a pharmaceutically acceptable salt thereof.

15. A compound as defined in claim 1 having the name (±)-1,2,3,6-tetrahydro-4-phenyl-1-(2-phenylethyl)-3-pyridinecarboxylic acid, methyl ester or a pharmaceutically acceptable salt thereof.

16. A compound as defined in claim 1 having the name (±)-1-ethyl-1,2,3,6-tetrahydro-4-phenyl-3-pyridinecarboxylic acid or a pharmaceutically acceptable salt thereof.

17. A compound as defined in claim 1 having the name (±)-1-ethyl-1,2,3,6-tetrahydro-4-phenyl-3-pyridinecarboxylic acid, cyclohexyl ester or a pharmaceutically acceptable salt thereof.

18. A compound as defined in claim 1 having the name (±)-1,2,3,6-tetrahydro-1-(cyclopentyl)-4-phenyl-3-pyridinecarboxylic acid, methyl ester or a pharmaceutically acceptable salt thereof.

19. A compound as defined in claim 1 having the name (±)-1-ethyl-1,2,3,6-tetrahydro-4-(4-nitrophenyl)-3-pyridinecarboxylic acid, methyl ester or a pharmaceutically acceptable salt thereof.

20. A pharmaceutical composition useful for alleviating the symtoms of senile cognitive decline comprising a cholinergically effective amount of a compound as defined in claim 1 together with a pharmaceutically acceptable carrier.

21. A method of alleviating the symptoms of senile cognitive decline comprising administering to a patient in need of such treatment a pharmaceutical composition as defined in claim 20.

* * * * *